(12) United States Patent
Uchida et al.

(10) Patent No.: US 7,605,361 B2
(45) Date of Patent: Oct. 20, 2009

(54) FUEL PROPERTY DETECTION DEVICE

(75) Inventors: Akikazu Uchida, Kariya (JP); Masao Kano, Gamagori (JP); Noriyasu Amano, Gamagori (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 0 days.

(21) Appl. No.: 12/170,023

(22) Filed: Jul. 9, 2008

(65) Prior Publication Data

US 2009/0015822 A1    Jan. 15, 2009

(30) Foreign Application Priority Data

Jul. 9, 2007    (JP)   ............... 2007-180167
Oct. 1, 2007    (JP)   ............... 2007-257837

(51) Int. Cl.
    *G01N 21/41*    (2006.01)
    *G01N 21/59*    (2006.01)
    *G01N 15/06*    (2006.01)
    *G02B 6/42*    (2006.01)

(52) U.S. Cl. ................. 250/227.25; 356/445; 356/135; 250/574; 250/208.1; 362/223

(58) Field of Classification Search ......... 356/128–137, 356/432–448; 250/573–574, 227.11, 227.24, 250/227.25, 208.1, 216, 234; 362/223, 225, 362/26

See application file for complete search history.

(56) References Cited

U.S. PATENT DOCUMENTS

| | | | |
|---|---|---|---|
| 5,126,570 A | | 6/1992 | Boos |
| 5,953,445 A | * | 9/1999 | Morikawa et al. ............ 382/141 |
| 5,998,782 A | * | 12/1999 | Koyama et al. ........ 250/227.25 |
| 6,017,130 A | * | 1/2000 | Saito et al. ................. 362/223 |
| 6,365,908 B1 | * | 4/2002 | Waigel et al. ............... 250/574 |
| 6,459,109 B2 | | 10/2002 | Takeshita et al. |
| 6,484,564 B1 | * | 11/2002 | Hayashida ..................... 73/40 |

(Continued)

FOREIGN PATENT DOCUMENTS

JP      62-276438      12/1987

(Continued)

OTHER PUBLICATIONS

Japanese Office Action dated May 26, 2009, issued in counterpart Japanese Application 2007-257837, with English translation.

*Primary Examiner*—Sang Nguyen
(74) *Attorney, Agent, or Firm*—Nixon & Vanderhye P.C.

(57) ABSTRACT

A fuel property detection device for detecting a property of fuel based on a detection signal output from a photoreceptor includes a light guiding member having a reflecting surface located in direct contact with the fuel. The light guiding member includes a light emitting surface through which measurement light from a light source is emitted from the light guiding member into the fuel, a light incident surface through which the measurement light emitted from the light emitting surface and passing through the fuel enters again the light guiding member, and the reflecting surface from which the measurement light incident from the light incident surface is reflected toward the photoreceptor. The light incident surface and the light emitting surface are opposite to each other to have a space therebetween in the light guiding member, and the space is provided to be filled with the fuel.

15 Claims, 5 Drawing Sheets

U.S. PATENT DOCUMENTS

| | | | |
|---|---|---|---|
| 7,309,873 B2 * | 12/2007 | Ishikawa | 250/574 |
| 7,339,150 B2 * | 3/2008 | Ohara | 250/208.1 |
| 2006/0076524 A1 | 4/2006 | Yoshigoe et al. | |
| 2007/0034785 A1 | 2/2007 | Yoshigoe et al. | |

FOREIGN PATENT DOCUMENTS

| | | |
|---|---|---|
| JP | 5-133886 | 5/1993 |
| JP | 2005-129832 | 5/2005 |
| JP | 2005-257319 | 9/2005 |

* cited by examiner

FUEL PROPERTY DETECTION DEVICE

CROSS REFERENCE TO RELATED APPLICATION

This application is based on Japanese Patent Applications No. 2007-180167 filed on Jul. 9, 2007, and No. 2007-257837 filed on Oct. 1, 2007, the contents of which are incorporated herein by reference in its entirety.

FIELD OF THE INVENTION

The present invention relates to an optical fuel property detection device for detecting the property of fuel, which includes a light source for irradiation of measurement light and a photoreceptor for receiving the measurement light.

BACKGROUND OF THE INVENTION

A conventional fuel property detection device as disclosed in, for example, JP-A-5-133886, is configured to cause light emitted from a light-emitting element to be reflected off a boundary surface of a prism in contact with gasoline, thereby detecting the degree of heaviness of the gasoline based on a change in output from a light-receiving element by using a correlation between the degree of heaviness of the gasoline and a refractive index thereof. The fuel property detection device also detects an alcohol concentration contained in the gasoline using a correlation between the alcohol concentration in the gasoline and an electrostatic capacity between a pair of electrodes.

The above-described fuel property detection device can detect the degree of heaviness of the gasoline and the alcohol concentration in the gasoline. The fuel property detection device, however, includes a gasoline heaviness degree detector with the light-emitting element and the light-receiving element, and an alcohol concentration detector with a pair of electrode plates. The fuel property detection device further includes two systems of electric circuits for controlling detecting operations of the respective detectors. Thus, the size of the fuel property detection device becomes large, and the electric circuits for control of the fuel property detection device become complicated.

SUMMARY OF THE INVENTION

The invention has been made in view of the foregoing problems, and it is an object of the invention to provide a fuel property detection device which can accurately detect the property of fuel with a simple structure.

It is an another object of the invention to provide a fuel property detection device which can accurately detect both a degree of heaviness of gasoline and an alcohol concentration contained in the gasoline, while reducing the size and number of components.

According to an aspect of the present invention, a fuel property detection device includes: a light guiding member disposed partially in contact with fuel and made of a translucent material, a light source disposed to allow light emitted therefrom to enter the light guiding member, a photoreceptor disposed to receive measurement light which is the light emitted from the light source and proceeding in the light guiding member, and a detection portion adapted to detect a property of the fuel based on the detection signal output from the photoreceptor. The light guiding member includes a light emitting surface through which the measurement light is emitted from the light guiding member into the fuel, a light incident surface through which the measurement light emitted from the light emitting surface and passing through the fuel enters again the light guiding member, and a reflecting surface at which the measurement light incident from the light incident surface is reflected toward the photoreceptor. Furthermore, the light incident surface and the light emitting surface are opposite to each other to have a space between the light emitting surface and the light incident surface in the light guiding member, the space is provided to be filled with the fuel, and the reflecting surface is in direct contact with the fuel.

With the above-described fuel property detection device, the measurement light emitted from the light source is emitted from the light emitting surface of the light guiding member into fuel, transmitted through the fuel, and then enters again the light guiding member from the incident surface. Thereafter, the light is reflected off the reflecting surface serving as an interface between the light guiding member and the fuel to enter the photoreceptor. Accordingly, the fuel property detection device can accurately detect the property of fuel with a simple structure. In the present invention, the translucent material has a light-transparent property, and includes a transparent material.

For example, the fuel may be gasoline including alcohol. In this case, the fuel property detection device may be configured to detect a degree of heaviness of the gasoline and a concentration of the alcohol contained in the gasoline. Accordingly, two types of information about the degree of heaviness of the gasoline and the alcohol concentration in the gasoline can be simultaneously measured using the one fuel property detection device that has the one light source and the one photoreceptor. Thus, the fuel property detection device can accurately detect both the degree of heaviness of the gasoline and the concentration of the alcohol contained in the gasoline, while reducing the size and number of components.

For example, the measurement light passes through the fuel between the light emitting surface and the light incident surface after being emitted from the light source and entering the light guiding member, and then may be totally reflected off the reflecting surface to enter the photoreceptor. In this case, the photoreceptor is capable of detecting a total amount of received light and an illuminance distribution at a light receiving area, and the photoreceptor can be disposed to allow the measurement light reflected off the reflecting surface to be incident thereinto. The photoreceptor may be a position sensitive detector (PSD), or/and the photoreceptor may include a plurality of phototransistors or photodiodes linearly arranged adjacent to each other. Furthermore, the light source may be a light emitting diode.

The fuel may be a liquid mixture of different kinds of fuel, and a wavelength range of the measurement light may be a near-infrared wavelength range.

In the fuel property detection device, the detection portion may include a storage means for previously storing a first map having a relationship between a refractive index of the fuel and a reflectivity of the reflecting surface, and a computation means for calculating a refractive index of the fuel and a transmittance of the fuel based on the first map stored in the storage means and the detection signal output from the photoreceptor. In this case, the computation means may further include: a refractive index calculation means for calculating the refractive index of the fuel based on the detection signal from the photoreceptor; a reflectivity calculation means for calculating the reflectivity on the reflecting surface based on the first map and the refractive index calculated by the refractive index calculation means; and a transmittance calculation means for calculating the transmittance of the fuel based on the reflectivity calculated by the reflectivity calculation means, the detection signal from the photoreceptor, and an amount of light emitted from the light source.

Alternatively, the detection portion may include: a storage means for previously storing a second map having a relationship between a refractive index of the fuel and a total amount of light received by the photoreceptor when a transmittance of the fuel is a predetermined value; and a computation means for calculating a refractive index of the fuel and a transmittance of the fuel based on the second map and the detection signal output from the photoreceptor. In this case, the computation means includes a refractive index calculation means for calculating the refractive index of the fuel based on the detection signal output from the photoreceptor, and a transmittance calculation means for calculating the transmittance of the fuel based on the second map, the refractive index calculated by the refractive index calculation means, and the detection signal from the photoreceptor.

In the fuel property detection device, the light emitting surface and the light incident surface may be parallel to each other to form the space therebetween in the light guiding member. In this case, the light emitting surface and the light incident surface can be configured such that an optical axis of the light passing through the light emitting surface and the light incident surface is substantially perpendicular to the light emitting surface and the light incident surface. Furthermore, the space may be provided in the light guiding member and may be open at the reflecting surface to communicate with a fuel path in which the fuel flows.

BRIEF DESCRIPTION OF THE DRAWINGS

Additional objects and advantages of the present invention will be more readily apparent from the following detailed description of preferred embodiments when taken together with the accompanying drawings. In which.

DETAILED DESCRIPTION OF THE PREFERRED EMBODIMENTS

First, preferred embodiments of the present invention will be now described. A fuel property detection device of the preferred embodiments includes: a light guiding member disposed partially in contact with fuel and made of a translucent material, a light source disposed to allow light emitted therefrom to enter the light guiding member, a photoreceptor disposed to receive measurement light which is the light emitted from the light source and proceeding in the light guiding member, and a detection portion adapted to detect a property of the fuel based on the detection signal output from the photoreceptor. The light guiding member includes a light emitting surface through which the measurement light is emitted from the light guiding member into the fuel, a light incident surface through which the measurement light emitted from the light emitting surface and passing through the fuel enters again the light guiding member, and a reflecting surface at which the measurement light incident from the light incident surface is reflected toward the photoreceptor. Furthermore, the light incident surface and the light emitting surface are opposite to each other to have a space between the light emitting surface and the light incident surface in the light guiding member, the space is provided to be filled with the fuel, and the reflecting surface is in direct contact with the fuel.

With the above-described fuel property detection device, the measurement light emitted from the light source is emitted from the light emitting surface of the light guiding member into fuel, transmitted through the fuel, and then enters the light guiding member from the incident surface. Thereafter, the light is reflected off the reflecting surface serving as an interface between the light guiding member and the fuel to enter the photoreceptor. Accordingly, the fuel property detection device can accurately detect the property of the fuel with a simple structure.

For example, the fuel is gasoline including alcohol. In this case, the detection portion may be configured to detect a degree of heaviness of the gasoline and a concentration of the alcohol contained in the gasoline. Accordingly, two types of information about the degree of heaviness of the gasoline and the alcohol concentration in the gasoline can be simultaneously measured using the one fuel property detection device that has the one light source and the one photoreceptor. Thus, the fuel property detection device can accurately detect both the degree of heaviness of the gasoline and the concentration of the alcohol contained in the gasoline, while reducing the size and number of components.

Now, the principle of detection of fuel properties, that is, the principle of detection of the degree of heaviness of the gasoline and of the alcohol concentration in the gasoline will be described below.

First, the principle of detection of the degree of heaviness of the gasoline will be described below. When the measurement light proceeding in the light guiding member enters the reflecting surface that is in direct contact with fuel, part of the measurement light whose incident angle on the reflecting surface is equal to or larger than a total reflection angle of the light guiding member is totally reflected off the reflecting surface to proceed in the light guiding member and then enters the photoreceptor. In contrast, the other part of the light whose incident angle on the reflecting surface is less than the total reflection angle is emitted from the reflecting surface into the fuel without entering the photoreceptor. The total reflection angle $\theta$ of the light guiding member is determined depending on a ratio of a refractive index N2 of the gasoline serving as a medium in contact with the reflecting surface to a refractive index N1 of the light guiding member. That is, the size of the total reflection angle $\theta A$ is represented by the following formula.

$$\sin \theta A = N2/N1$$

Furthermore, a relationship between the degree of heaviness of the gasoline and the refractive index thereof is as follows: the larger the degree of heaviness of the gasoline, the larger the refractive index. This relationship and the above formula show that the higher the degree of heaviness of the gasoline, the larger the total reflection angle on the reflecting surface of the light guiding member.

As mentioned above, only part of the measurement light whose incident angle on the reflecting surface is equal to or larger than the total reflection angle at the light guiding member is totally reflected off the reflecting surface to proceed in the light guiding member and then enters the photoreceptor. That is, the incident angle of the measurement light entering the photoreceptor is set in a certain range of angle. In other words, an incident area where the measurement light in a light receiving area of the photoreceptor enters is limited to a given range. When the degree of heaviness of the gasoline in contact with the reflecting surface changes to allow the total reflection angle on the reflecting surface to be changed, the incident area of the measurement light in the light receiving area of the photoreceptor changes. The photoreceptor included in the fuel property detection device can detect illuminance distribution in the light receiving area. Thus, the degree of heaviness of the gasoline can be detected based on a detection signal from the photoreceptor, that is, an illuminance distribution detection signal in the light receiving area.

Next, the principle of detection of the alcohol concentration contained in the gasoline will be described below.

An OH group of the alcohol has an action of absorbing light in a specific range of frequency, specifically, light in an infrared frequency region. Thus, when the light emitted from the light source passes through the alcohol, the amount of light having passed through the alcohol is decreased as compared to the amount of light just emitted from the light source. In contrast, when the light emitted from the light source passes through the gasoline, light is hardly absorbed, so that the amount of light having passed through the gasoline is not decreased. Thus, the amount of light transmitted from the light source through a liquid mixture of the gasoline and alcohol becomes maximum for a gasoline concentration of 100%, that is, an alcohol concentration of 0%. As the alcohol concentration of the gasoline is increased, the amount of transmitted light is decreased. The amount of light emitted from the light source can be previously determined from light emitting characteristics of the light source, a driving current condition, or the like. The light from the light source is allowed to be transmitted through the liquid mixture of the gasoline and alcohol charged into the space between the light emitting surface and the light incident surface of the light guiding member and then the amount of the transmitted light is measured, so as to detect an alcohol concentration in the liquid mixture.

The photoreceptor included in the fuel property detection device of the invention can detect the total amount of light received at the light receiving area. The amount of the received light detected by the photoreceptor is determined by subtracting an amount of light absorbed by alcohol contained in the fuel when the light passes through the fuel filled in the space between the light emitting surface and the light incident surface of the light guiding member and an amount of light emitted into the fuel, from an amount of light emitted from the light source. This is based on the fact that the incident angle on the reflecting surface in contact with the fuel is smaller than the total reflection angle. The illuminance distribution detection signal in the light receiving area of the photoreceptor corresponding to the degree of heaviness of the gasoline is constant regardless of a change in amount of light received at the light receiving area when the degree of heaviness of the gasoline is constant. Thus, the degree of heaviness of the gasoline can be detected based on the illuminance distribution detection signal at the light receiving area, apart from the alcohol concentration in the gasoline. Then, as to the alcohol concentration in the gasoline, a relationship between the total amount of light received at the light receiving area of the photoreceptor and the alcohol concentration is previously measured with respect to the degree of heaviness of various types of gasoline, and then is prepared as data. The alcohol concentration can be determined with reference to the data. That is, first, the degree of heaviness of the gasoline is detected based on the illuminance distribution detection signal from the photoreceptor. Subsequently, the alcohol concentration in the gasoline can be detected based on a detection signal indicative of the total amount of light received at the photoreceptor and on data indicative of the relationship between the alcohol concentration and the total received-light amount at the light receiving area of the photoreceptor in the liquid mixture of the alcohol and the gasoline having the degree of heaviness detected.

As mentioned above, two types of information about the degree of heaviness of the gasoline and the alcohol concentration in the gasoline can be simultaneously measured using the one fuel property detection device having the one light source and the one photoreceptor. Thus, the fuel property detection device can accurately detect both the degree of heaviness of the gasoline and the concentration of the alcohol contained in the gasoline, while reducing the size and number of components.

A liquid mixture of different kinds of fuel, for example, a liquid mixture of gasoline and alcohol may be used. In this case, the alcohol selectively absorbs light in a near-infrared wavelength range. In contrast, the gasoline allows the light in the wavelength range to completely pass therethrough. Thus, when the fuel consists of a liquid mixture of gasoline and alcohol, the use of light in the near-infrared wavelength range as the measurement light can detect the alcohol concentration with high accuracy.

The detection portion may include a storage means for previously storing a first map having a relationship between a refractive index of the fuel and a reflectivity of the reflecting surface, and a computation means for calculating a refractive index of the fuel and a transmittance of the fuel based on the first map stored in the storage means and the detection signal output from the photoreceptor.

The measurement light emitted from the light source enters the reflecting surface of the light guiding member after being transmitted through the fuel at a midway point, and then is reflected off the reflecting surface of the light guiding member to enter the photoreceptor. With this arrangement, the amount of measurement light entering the photoreceptor can be determined by subtracting the amount of light absorbed by the fuel during transmission of the light through the fuel and the amount of light emitted into the fuel upon the reflecting surface from the amount of light emitted from the light source.

When the measurement light is incident on the reflecting surface, a total reflection angle is determined by the refractive index of the fuel. When the refractive index of the fuel changes, the total reflection angle is also changed therewith, which leads to a change in amount of light emitted from the reflecting surface into the fuel. In other words, the amount of light totally reflected off the reflecting surface to proceed toward the photoreceptor is changed, so as to change the amount of light received by the photoreceptor and the luminance distribution of the received light amount at the photoreceptor.

When the refractive index of the fuel is constant and only the transmittance of the light through the fuel changes, the amount of light received by the photoreceptor is changed, but the illuminance distribution of the incident light on the photoreceptor does not change. Thus, the refractive index of the fuel can be calculated based on the illuminance distribution of the incident light on the photoreceptor. By verifying the calculated refractive index against the first map, a reflectivity of the reflecting surface of the light guiding member can be determined. The amount of light incident on the reflecting surface, that is, the amount of measurement light having passed through the fuel can be calculated based on the reflectivity and the amount of light received at the photoreceptor. Furthermore, the light transmittance of the fuel can be calculated based on the amounts of the measurement light before and after passing through the fuel, that is, based on the amount of light emitted from the light source. The amount of measurement light before passing through the fuel can be previously determined from the light emitting characteristics and the driving current condition of the light source, or the like. Thus, a transmittance of the fuel can be calculated based on the amount of light incident on the reflecting surface which is calculated by the computation means and the amount of light emitted from the light source. A degree of heaviness of the gasoline and an alcohol concentration can be calculated based on the calculated refractive index and on the transmittance described above, respectively.

For example, the computation means further includes: a refractive index calculation means for calculating the refractive index of the fuel based on the detection signal from the photoreceptor; a reflectivity calculation means for calculating the reflectivity on the reflecting surface based on the first map and the refractive index calculated by the refractive index calculation means; and a transmittance calculation means for calculating the transmittance of the fuel based on the reflectivity calculated by the reflectivity calculation means, the detection signal from the photoreceptor, and an amount of light emitted from the light source.

Alternatively, the detection portion may include a storage means for previously storing a second map having a relationship between a refractive index of the fuel and a total amount of light received by the photoreceptor when a transmittance of the fuel is a predetermined value; and a computation means for calculating a refractive index of the fuel and a transmittance of the fuel based on the second map and the detection signal output from the photoreceptor.

The measurement light emitted from the light source enters the reflecting surface of the light guiding member at a midway point after being transmitted through the fuel to be reflected off the reflecting surface, and then enters the photoreceptor. With this arrangement, the amount of measurement light entering the photoreceptor can be determined by subtracting the amount of light absorbed by the fuel during transmission of the light through the fuel and the amount of light emitted into the fuel on the reflecting surface from the amount of light emitted from the light source.

When the measurement light is incident on the reflecting surface, the total reflection angle can be determined by the refractive index of the fuel. When the refractive index of the fuel changes, the total reflection angle is also changed therewith, which leads to a change in amount of light emitted from the reflecting surface into the fuel. In other words, the amount of light totally reflected off the reflecting surface to proceed toward the photoreceptor is changed, thereby changing the amount of light received by the photoreceptor and the luminance distribution of the received light amount at the photoreceptor.

When the refractive index of the fuel is constant and only the light transmittance of the fuel changes, the amount of light received by the photoreceptor is changed, but the illuminance distribution of the incident light on the photoreceptor does not change. Thus, the refractive index of the fuel can be calculated based on the illuminance distribution of the incident light on the photoreceptor.

When the refractive index of the fuel is constant, the amount of light incident on the photoreceptor changes only according to the amount of light absorbed by the fuel in transmission of the light through the fuel, that is, the amount of light absorbed. In other words, the incident light amount changes only depending on the transmittance of the light through the fuel. Thus, the amount of light incident on the photoreceptor with the refractive index of the fuel being constant becomes maximum when the light transmittance of the fuel is 100%. As the fuel transmittance is decreased from 100%, the incident light amount is also decreased. That is, the light transmittance of the fuel can be calculated by computing the ratio of the amount of light actually received by the photoreceptor to the amount of light incident on the photoreceptor estimated when the light transmittance of the fuel is known at the refractive index calculated based on the illuminance distribution of the light incident on the photoreceptor.

In this way, the degree of heaviness of the gasoline and the alcohol concentration can be calculated based on the refractive index and on the transmission calculated as described above, respectively.

In this case, the computation means may include a refractive index calculation means for calculating the refractive index of the fuel based on the detection signal output from the photoreceptor, and a transmittance calculation means for calculating the transmittance of the fuel based on the second map, the refractive index calculated by the refractive index calculation means, and the detection signal from the photoreceptor. Accordingly, the refractive index of the fuel and the transmittance of the fuel can be accurately calculated.

EMBODIMENT AND MODIFIED EXAMPLES THEREOF

A specific embodiment and modified examples of a fuel property detection device according to the invention will be described below with reference to the accompanying drawings by taking an example in which the fuel property detection device is used as a fuel property sensor 1 for a vehicle.

Figure 1:
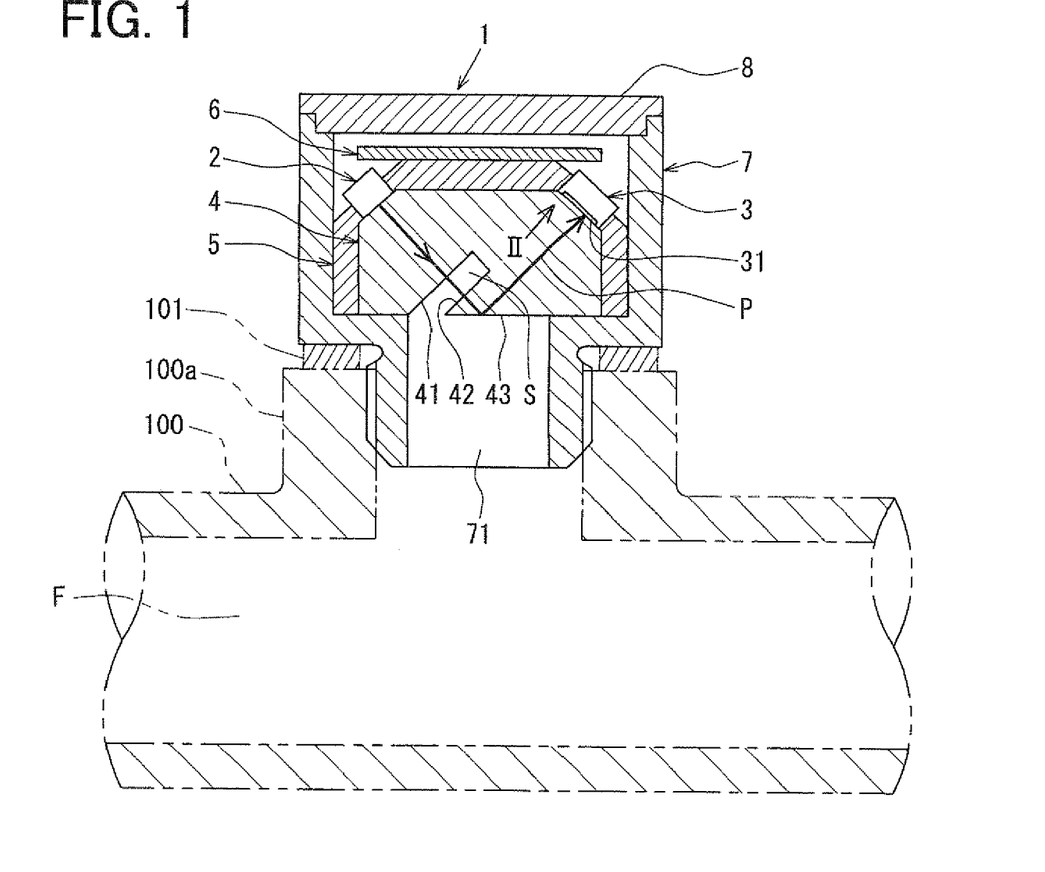
FIG. 1 is a cross sectional view of a fuel property sensor according to an embodiment of the invention.

The fuel property sensor 1 is attached to a fuel piping 100 for supplying fuel in a fuel tank (not shown) to an engine (not shown), as shown in FIG. 1. That is, the fuel property sensor 1 is fixed by screw connection to a boss portion 100*a* provided in the fuel piping 100 via a gasket 101. While fuel F flows through the fuel piping 100, the fuel F flows into the fuel property sensor 1.

The fuel F used is a liquid mixture of gasoline and ethanol that is an example of alcohol. The fuel F has wide variations in content ratio of a heavy component in the gasoline, and variations in concentration of the ethanol contained. For example, the heavy component of the gasoline is an aroma component, an olefin component, or the like. Hereinafter, the content ratio of a heavy component in the gasoline is referred to as a "degree of heaviness". Thus, in order to drive the vehicle so as to constantly bring the engine (not shown) in an appropriate state, for example, to minimize the amounts of toxic substances in exhaust gas while generating a desired torque using the fuel F in which the content of the heavy component is varied in a wide range, the following means is necessary. That is, fuel properties, for example, the degree of heaviness of the gasoline, and the concentration of the ethanol contained in the gasoline are detected by some means such as the fuel property sensor 1, and then the amount of injection of the fuel, the timing of fuel injection and the like are appropriately controlled based on the detected fuel properties.

The configuration of the fuel property sensor 1 according to the invention will be described below.

The fuel property sensor 1 mainly includes a light guiding member 4 disposed to have a part thereof immersed in the fuel F, a light emitting diode 2 disposed to allow light to enter the light guiding member 4, a position sensitive detector (PSD) 3 disposed to allow the light proceeding from the light emitting diode 2 through the light guiding member 4 to be incident therein, and a housing 7 for accommodating and holding therein those components.

The light guiding member 4 is formed of glass, which is translucent material, in a substantially block shape. The translucent material has a light-transparent property, and includes a transparent material. The light guiding member 4 includes a light emitting surface 41 from which the measurement light emitted from the light emitting diode 2 to enter the light guiding member 4 is emitted into the fuel F, and a light incident surface 42 via which the measurement light emitted from the light emitting surface 41 and passing through the fuel F again enters the light guiding member 4. The light guiding member 4 also includes a reflecting surface 43 from which the measurement light entering the light guiding member 4 from the incident surface 42 is reflected toward the PSD 3.

The light emitting surface 41 and the light incident surface 42 are formed in parallel so as to be opposed to each other as shown in FIG. 1. That is, the light emitting surface 41 and the light incident surface 42 are formed as wall surfaces constituting a recess S. The recess S is provided in the light guiding member 4. In a state where the fuel property sensor 1 is attached to the fuel piping 100 of the vehicle, the recess S is filled with the fuel F, while the fuel is in contact with the reflecting surface 43. For example, the reflecting surface 43 of the light guiding member 4 is immersed in the fuel F so as to contact the fuel F.

The light emitting diode 2 used as a light source has a center wavelength of the emitted light of about 1600 nm. This is based on the following reasons. Since the light having a wavelength of about 1600 nm is not absorbed by the gasoline, the transmittance of light through the gasoline is about 100%. In contrast, since the light having such a wavelength is absorbed by the ethanol, the transmittance of the light through ethanol is low. In a case where the light having such a wavelength is used as the measurement light, when the fuel F consists of 100% gasoline, the transmittance of the measurement light through the fuel F, that is, the amount of measurement light passing through the fuel F becomes maximum. As the ethanol concentration contained in the fuel F is increased, the transmittance of the measurement light through the fuel F, that is, the amount of the measurement light passing through the fuel F is decreased. Applications for detecting an ethanol concentration of a liquid mixture consisting of gasoline and ethanol preferably employ light having a wavelength at which the light transmittance of the gasoline is about 100% and the light transmittance of the ethanol is as low as possible. The light emitting diode 2 has a light emitting surface that is disposed to contact the light guiding member 4. This allows 100% of the light emitted from the light emitting diode 2 to be incident into the light guiding member 4, thereby increasing the amount of measurement light to enhance the accuracy of detection of the fuel property. The light is emitted radially from the light emitting diode 2, but an optical path in which the brightness of light is maximum is an optical axis P. In the fuel property sensor 1 of an embodiment of the invention, the light emitting diode 2 is disposed to make the optical axis P thereof substantially perpendicular to the light emitting surface 41 and the light incident surface 42 of the light guiding member 4. This can minimize the loss of light due to a light leak that may occur when the measurement light passes through the light emitting surface 41 and the light incident surface 42.

Figure 2:
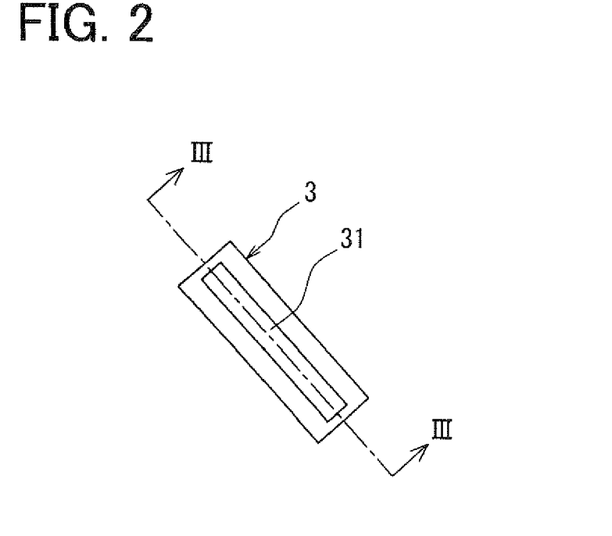
FIG. 2 is a diagram as being viewed along the arrow II in FIG. 1.
Figure 3:
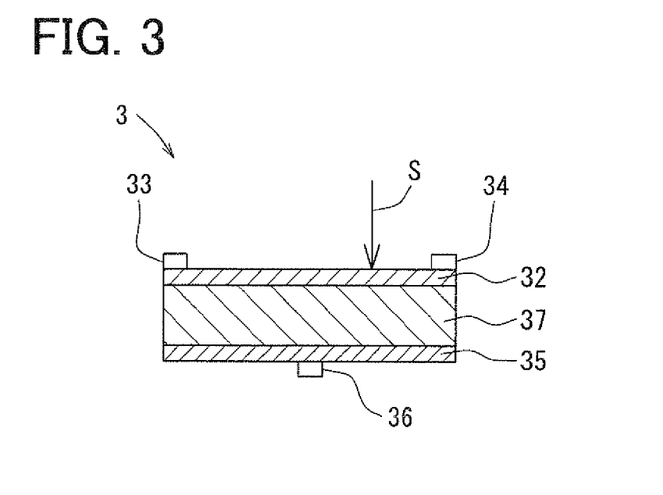
FIG. 3 is a cross sectional view taken along the line III-III in FIG. 2.

The PSD 3 used as the photoreceptor is a one-dimensional PSD. As shown in FIG. 2, the PSD 3 includes a strip-like detection surface 31. Now, the structure of the PSD 3 and the light detection operation performed by the PSD 3 will be described below. As shown in FIG. 3, the PSD 3 has the same structure as that of a PIN type photodiode, and thus a P layer 32 forms a detection surface. The P layer 32 has a pair of output electrodes 33 and 34 formed on both ends thereof. A common electrode 36 is formed on an N layer 35. An I layer (intrinsic semiconductor layer) 37 is provided between the P layer 32 and the N layer 35. As shown in FIG. 3, when a spotlight S enters the detection surface 31 of the PSD 3, electric charges in proportion to the amount of light occur in an incident position, and then reaches the P layer 32 as a photocurrent. The electric charges are divided in inverse proportion to distances to the respective output electrodes 33 and 34 to be derived from the output electrodes 33 and 34. An output current I33 of the output electrode 33 and an output current I34 of the output electrode 34 can be measured to calculate the incident position of the spotlight S, that is, a distance from the output electrode 33 or 34 to the incident position. The amount of light incident on the detection surface 31 can be calculated based on the total photocurrent I0 which is the sum of the output current I33 and the output current I34. When the light incident on the detection surface 31 is not a spotlight S and enters a certain area of the detection surface 31, the incident position calculated based on the output currents I33 and I34 corresponds to a barycenter of the amount of incident light.

The light guiding member 4, the light emitting diode 2, and the PSD 3 mentioned above are integrally held and fixed together via a holder 5 as shown in FIG. 1. The holder 5 is formed of, for example, resin material or the like. A circuit board 6 is attached to the holder 5. The circuit board 6 has electric circuits (not shown) formed for performing lighting driving control of the light emitting diode 2, detection signal processing of a detection signal from the PSD 3, and incident light position calculation processing.

The holder 5 for integrally holding and fixing the light guiding member 4, the light emitting diode 2, and the PSD 3 and the circuit board 6 are accommodated and fixed into the housing 7 as shown in FIG. 1. The housing 7 is formed of, for example, metallic material or the like. The housing 7 has a communication hole 71 whose one end is opened and which faces the light guiding member 4. As shown in FIG. 1, a cover 8 is mounted on the end of the housing 7 opposite to the communication hole 71. The cover 8 hermetically protects the light guiding member 4, the light emitting diode 2, the PSD 3, and the circuit board 6 in the housing 7. The cover 8 is provided with an electric connector (not shown), which is electrically connected to the circuit board 6. Connecting the electric connector (not shown) to external electric wiring allows the fuel property sensor 1 to be connected to an external electric circuit.

The fuel property sensor 1 is attached to the fuel piping 100 via the housing 7. That is, as shown in FIG. 1, the fuel property sensor 1 is fixed by screw fastening means to the boss portion 100a provided in the fuel piping 100 via the gasket 101. When the fuel property sensor 1 is fixed to the fuel piping 100, the fuel F in the fuel piping 100 leads to the light guiding member 4 via the communication hole 71 so that the light guiding member 4 is immersed in the fuel F. That is, the recess S of the light guiding member 4 is filled with the fuel F, and the fuel F is brought into direct contact with the reflecting surface 43.

Now, the operation of the fuel property sensor 1 with the above-described structure according to the embodiment of the invention, that is, the fuel property detection operation of the sensor 1 will be described in detail below.

In the fuel property sensor 1 of the embodiment of the invention, the light emitted from the light emitting diode 2, that is, the measurement light proceeds as indicated by the arrow in FIG. 1 to enter the PSD 3. That is, after proceeding in the light guiding member 4, the light is emitted from the light emitting surface 41 into the fuel F to be transmitted through the fuel F, and then to enter the light guiding member 4 again from the light incident surface 42. The light proceeds in the light guiding member 4 to be reflected off the reflecting surface 43, and then enters the detection surface 31 of the PSD 3.

In a route in which the measurement light emitted from the light emitting diode 2 is received by the PSD 3, especially, in a route in which the measurement light having passed through the fuel F is reflected off the reflecting surface 43 to lead to the PSD 3, the reflection of the measurement light from the reflecting surface 43 will be first described below. When the measurement light is incident on the reflecting surface 43, part of the measurement light whose incident angle θ with respect to the reflecting surface 43 is equal to or larger than the total reflection angle of the reflecting surface 43 is totally reflected off the reflecting surface 43 to enter the PSD 3. In contrast, the other part of the measurement light whose incident angle θ with respect to the reflecting surface 43 is less than the total reflection angle of the reflecting surface 43 is emitted from the reflecting surface 43 toward the outside of the light guiding member 4, that is, into the fuel F.

The total reflection angle θA on the reflecting surface 43, which is an interface between the light guiding member 4 and the fuel F, is determined depending on a medium in contact with the light guiding member 4, that is, on the refractive index of the fuel F. The total reflection angle θA on the reflecting surface 43 changes with a change in refractive index of the fuel F. When N1 indicates the refractive index of the light guiding member 4 and N2 indicates the refractive index of the gasoline, the size of the total reflection angle θA is represented by the following formula (1).

$$\sin \theta A = N2/N1 \quad (1)$$

Furthermore, the relationship between the degree of heaviness of the gasoline and the refractive index N2 of the gasoline is as follows: the larger the degree of heaviness of the gasoline, the larger the refractive index. This relationship and the above formula (1) show that the higher the degree of heaviness of the gasoline, the larger the total reflection angle θA on the reflecting surface 43 of the light guiding member 4.

Thus, when the degree of heaviness of the gasoline changes in the fuel F, the total reflection angle θA on the reflecting surface 43 is changed. Together with this, an incident area and an incident light amount on the detection surface 31 of the PSD 3 of the measurement light reflected off the reflecting surface 43 to proceed toward the PSD 3 are also changed. This phenomenon will be described below with reference to FIG. 4.

Figure 4:
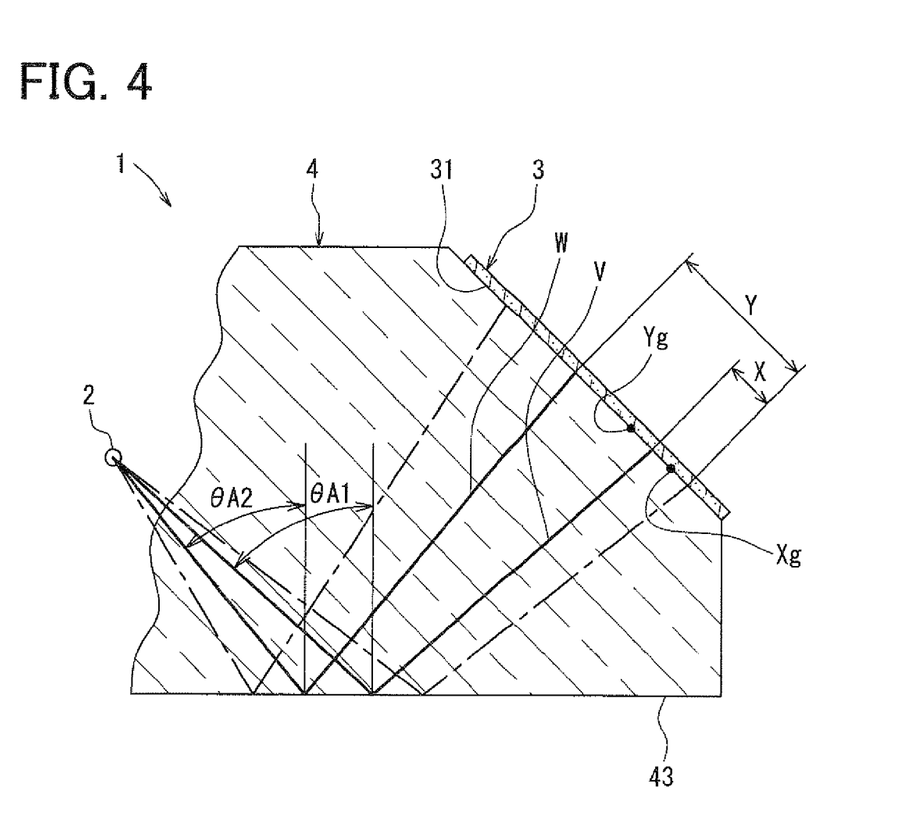
FIG. 4 is a schematic diagram for explaining an optical path of measurement light upon a reflecting surface and a state of the light incident on a PSD 3.

The measurement light is emitted radially in a conical manner with the light emitting diode 2 being centered. FIG. 4 shows a cross section including an optical axis of the light emitted from the light emitting diode 2, that is, an optical path of the light whose brightness is maximum. In FIG. 4, optical paths having both ends of a distribution range of the radial measurement light are represented by the alternate long and short dashed line. Suppose the degree of heaviness of the gasoline is decreased to change the total reflection angle from an angle θA1 to an angle θA2. It is noted that θA1>θA2. In FIG. 4, the optical path at the total reflection angle θA1 is indicated by an optical path V, and the optical path at the total reflection angle θA2 is indicated by an optical path W. In the measurement light incident on the reflecting surface 43, part of the light whose incident angle with respect to the reflecting surface 43 is equal to or larger than the total reflection angle θA enters the PSD 3. Thus, as shown in FIG. 4, an incident area of the measurement light on the detection surface 31 of the PSD 3 is an incident area X for the total reflection angle θA1, or an incident area Y for the total reflection angle θA2. The barycenter of the light amount at the incident area X is a light amount barycenter Xg, and the barycenter of the light amount at the incident area Y is a light amount barycenter Yg. In the fuel property sensor 1, the above-described light amount barycenters Xg and Yg are calculated based on the detection signals from the PSD 3. The light amount barycenters Xg and Yg have a correlation with respect to the degrees of heaviness of the gasoline. Thus, the light amount barycenter of the measurement light is calculated based on an output signal from the PSD 3 when receiving the measurement light. Then, the degree of heaviness of the gasoline can also be detected with reference to the relationship between the light amount barycenter calculated and the degree of heaviness of the gasoline previously measured. The PSD 3 is disposed to surely enable receiving the measurement light even when the incident area of the measurement light is varied in response to fluctuations in degree of heaviness of the gasoline. That is, in the fuel property sensor 1 of the embodiment of the invention, one dimensional PSD is used as the PSD 3, and disposed such that the expanding direction of the detection area (longitudinal direction) is aligned along the sectional view shown in FIG. 4, that is, the cross section including the optical axis of the light emitting diode 2.

Next, a route in which the measurement light emitted from the diode 2 is transmitted through the fuel F from the light guiding member 4 and proceeds in the light guiding member 4 again to lead to the reflecting surface 43 will be described in detail. When the measurement light proceeds in the light guiding member 4, there is little loss in light amount. In contrast, when the light is transmitted through the fuel F, the measurement light is absorbed by ethanol contained in the fuel F, resulting in a decrease in amount of the measurement light. That is, the higher the concentration of ethanol contained in the fuel F, the higher the degree of decrease in amount of the measurement light having passed through the fuel F. Thus, measuring of the amount of the measurement light having passed through the fuel F can detect the ethanol concentration based thereon. In the fuel property sensor 1 of the embodiment of the invention, even when the measurement light having passed through the fuel F is subsequently reflected off the reflecting surface 43, part of the measurement light is emitted from the reflecting surface 43 toward the outside, which further leads to a decrease in amount of the light. For this reason, the decreased amount of the measurement light measured based on the light amount received by the PSD 3 is the sum of the amount of light absorbed by ethanol and the amount of light emitted from the reflecting surface 43 toward the outside, both of which cannot be separately measured. Thus, the relationship between the amount of light detected by the PSD 3 and the ethanol concentration is previously measured for each degree of heaviness of every type of gasoline. First, the degree of heaviness of the gasoline is detected based on the barycenter of the amount of the measurement light detected by the PSD 3. Then, an ethanol concentration is calculated with reference to the relationship between the ethanol concentration and the light amount received by the PSD 3 at the degree of heaviness of the gasoline detected.

According to the fuel property sensor 1 with the above-described arrangement in the one embodiment of the invention, a pair of detection means, namely, the light emitting diode 2 and the PSD 3 are provided. The ethanol concentration is detected from the amount of light received by the PSD 3, and from the correlation between the degree of decrease in amount of the measured light having passed through the fuel and the alcohol concentration. The degree of heaviness of the gasoline is detected from the barycenter of the light amount in the PSD 3 and from the correlation between the degree of heaviness of the gasoline and the total reflection angle. Thus, the degree of heaviness of the gasoline and the ethanol concentration, which are two types of property data regarding the fuel F, can be detected with high accuracy using the light emitting diode 2 and the PSD 3 which are the pair of detection means.

A conventional fuel property detection device includes two detection means for detection of the degree of heaviness of the gasoline and for detection of an alcohol concentration in the gasoline, and thus has a large size. Further, the detection device has to perform signal processing for two systems, and thus has complicated electric circuits for controlling the fuel property detection device.

In contrast, according to the fuel property sensor 1 of the embodiment of the invention, two types of information about the degree of heaviness of the gasoline and the alcohol concentration in the gasoline can be simultaneously measured using the light emitting diode 2 and the PSD 3 which are one pair of detection means. This can achieve the fuel property sensor 1 which can accurately detect both the degree of heaviness of the gasoline and the alcohol concentration contained in the gasoline, while reducing the size and number of the components thereof.

Figure 5:
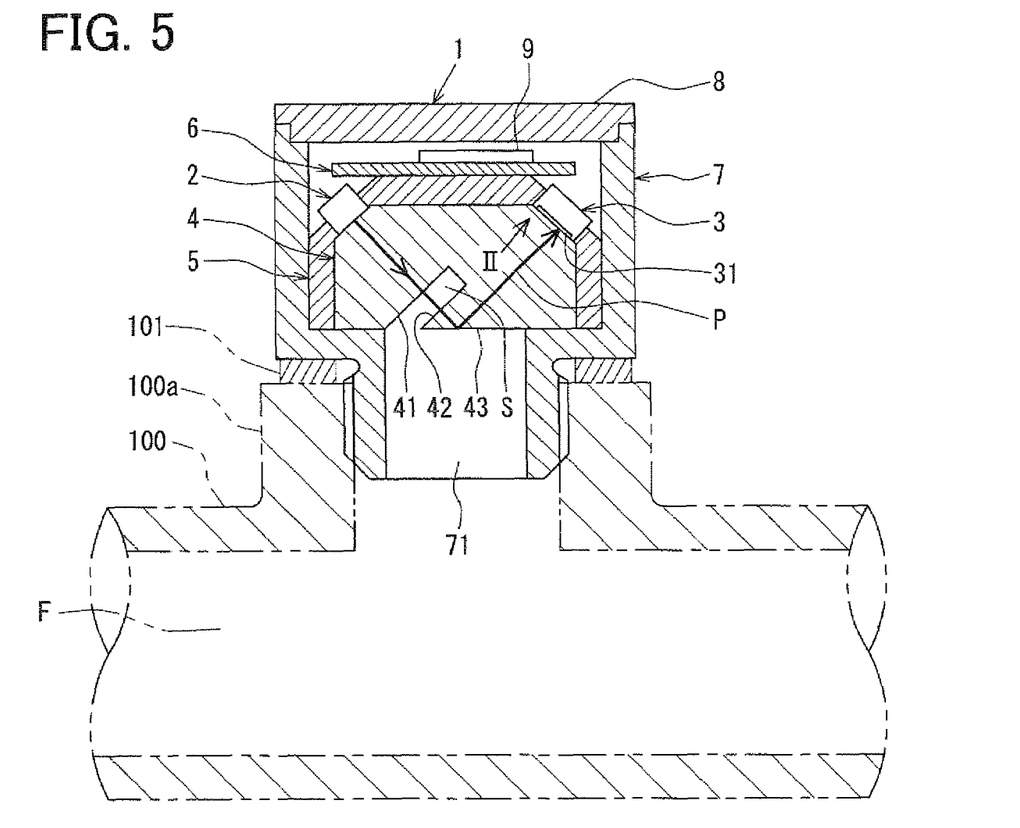
FIG. 5 is a cross sectional view showing a fuel property sensor according to a modified example of the embodiment of the invention.

Next, the fuel property detection operation performed by using a fuel property sensor 1 according to a modified example of the embodiment of the invention will be described with reference to FIG. 5. As shown in FIG. 5, in the modified example, the microcomputer 9 serves as electric circuits is mounted on the circuit board 6. The microcomputer 9 is configured to perform a lighting driving control of the light emitting diode 2, detection signal processing of a detection signal from the PSD 3, incident light position calculation processing, and the like.

Figure 6:
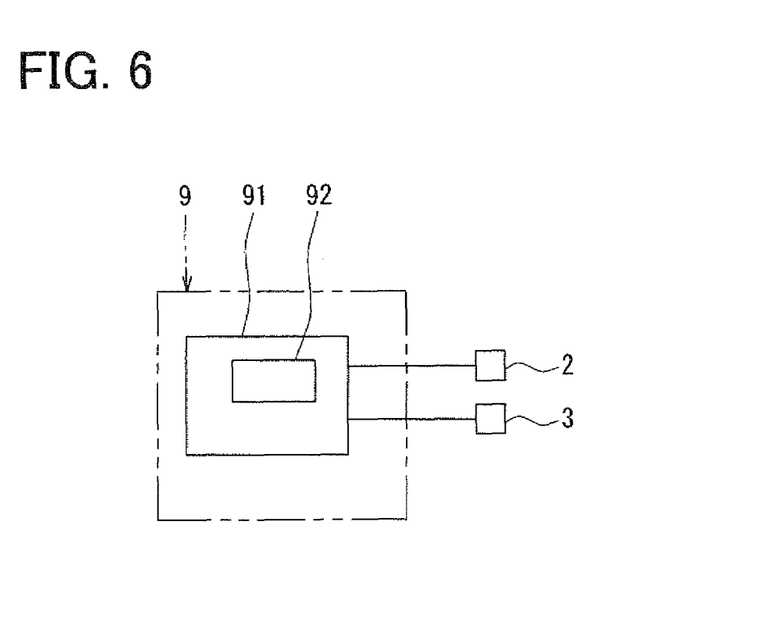
FIG. 6 is a block diagram of a microcomputer.

The microcomputer 9 includes computation means 91 as shown in the block diagram in FIG. 6. The light emitting diode 2 is connected to the computation means 91 so as to be capable of detecting driving current thereof, and the PSD 3 is also connected to the computation means 91 so as to be capable of inputting a detection signal, as shown in FIG. 6. The computation means 91 further includes a storage area 92. The storage area 92 previously stores therein data serving as a first map, that is, data about a relationship between the refractive index of the fuel F and the reflectivity of the reflecting surface 43.

Figure 7:
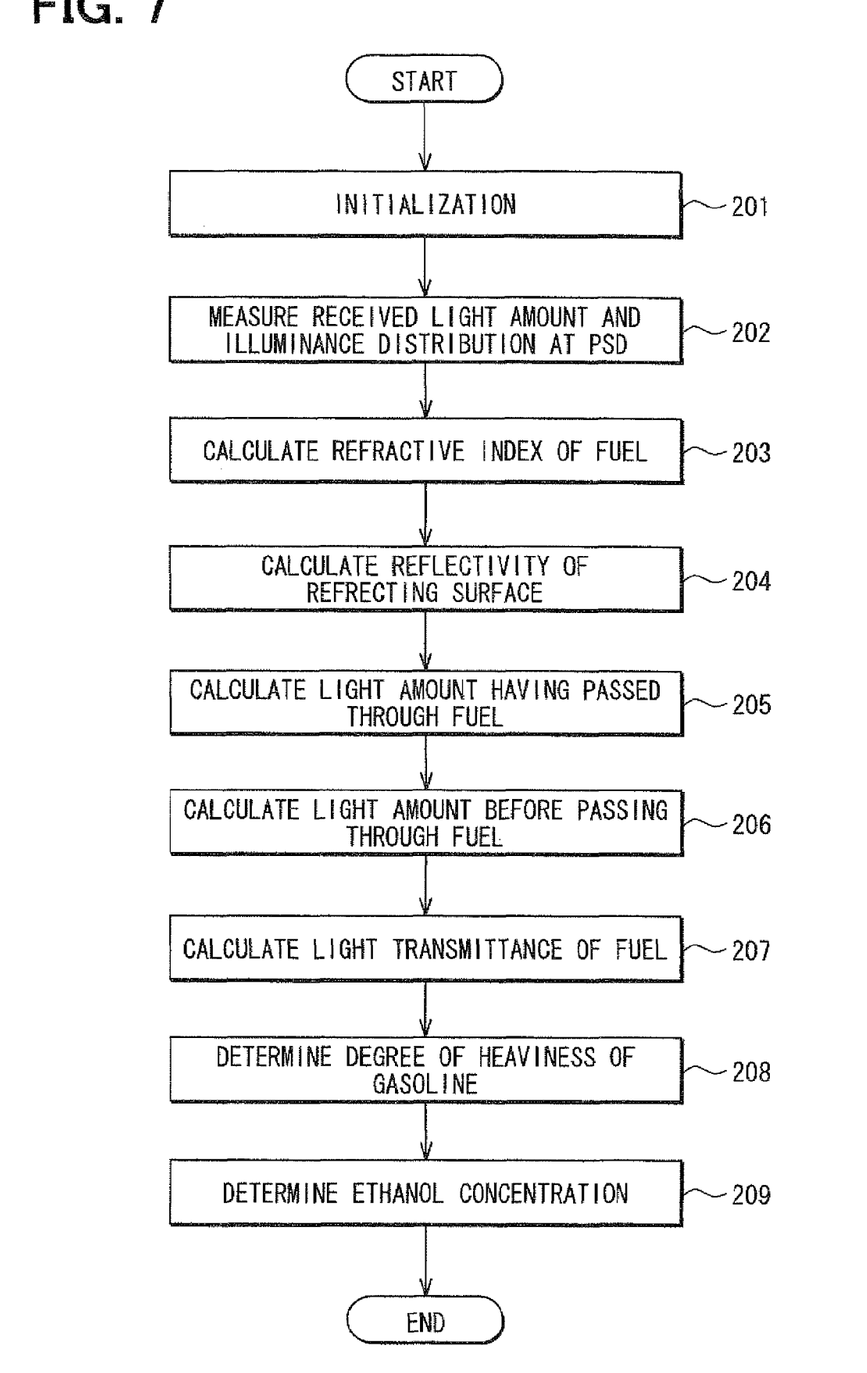
FIG. 7 is a flowchart of a fuel property detection procedure performed by the microcomputer.

A fuel property detection procedure performed by the computation means 91 will be described below based on the flowchart shown in FIG. 7.

When an ignition switch (switch) of a vehicle 100 is turned ON by a driver's operation, the fuel property sensor 1 starts to be operated, and then the computation means 91 of the microcomputer 9 starts the fuel property detection procedure. The computation means 91 first performs initialization in step S201.

Subsequently, in step S202, the computation means 91 measures the amount of received light and the illuminance distribution (i.e., barycenter of receiving light) at the PSD 3.

Then, in step S203, the computation means 91 calculates the refractive index of the fuel based on the light receiving barycenter of the PSD 3 measured in step S202.

Subsequently, in step S204, the computation means 91 calculates the reflectivity of the reflecting surface 43 of the light guiding member 4 based on the refractive index of the fuel calculated in step S203 and on the first map stored in the storage area 92, that is, data about the relationship between the refractive index of the fuel F and the reflectivity of the reflecting surface 43.

Thereafter, in step S205, the computation means 91 calculates the amount of light incident on the reflecting surface 43, that is, the amount of light having passed through the fuel F based on the reflectivity of the reflecting surface 43 of the light guiding member 4 calculated in step S204 and the amount of received light of the PSD 3 measured in step S202.

Subsequently, in step S206, the computation means 91 calculates the amount of light emitted from the light emitting diode 2, that is, the amount of light before passing through the fuel F, based on a driving current of the light emitting diode 2.

Then, in step S207, the computation means 91 calculates the light transmittance of the fuel F based on the amount of light having passed through the fuel F, which has been calculated in step S205, and the amount of light before passing through the fuel F, which has been calculated in step S206.

Subsequently, in step S208, the computation means 91 determines the degree of heaviness of the fuel F, that is, the degree of heaviness of the gasoline based on the refractive index of the fuel F calculated in step S203.

Then, in step S209, the computation means 91 determines the ethanol concentration of the fuel F based on the light transmittance of the fuel F calculated in step S207.

By the procedure described above, the properties of the fuel F can be determined.

Figure 8:
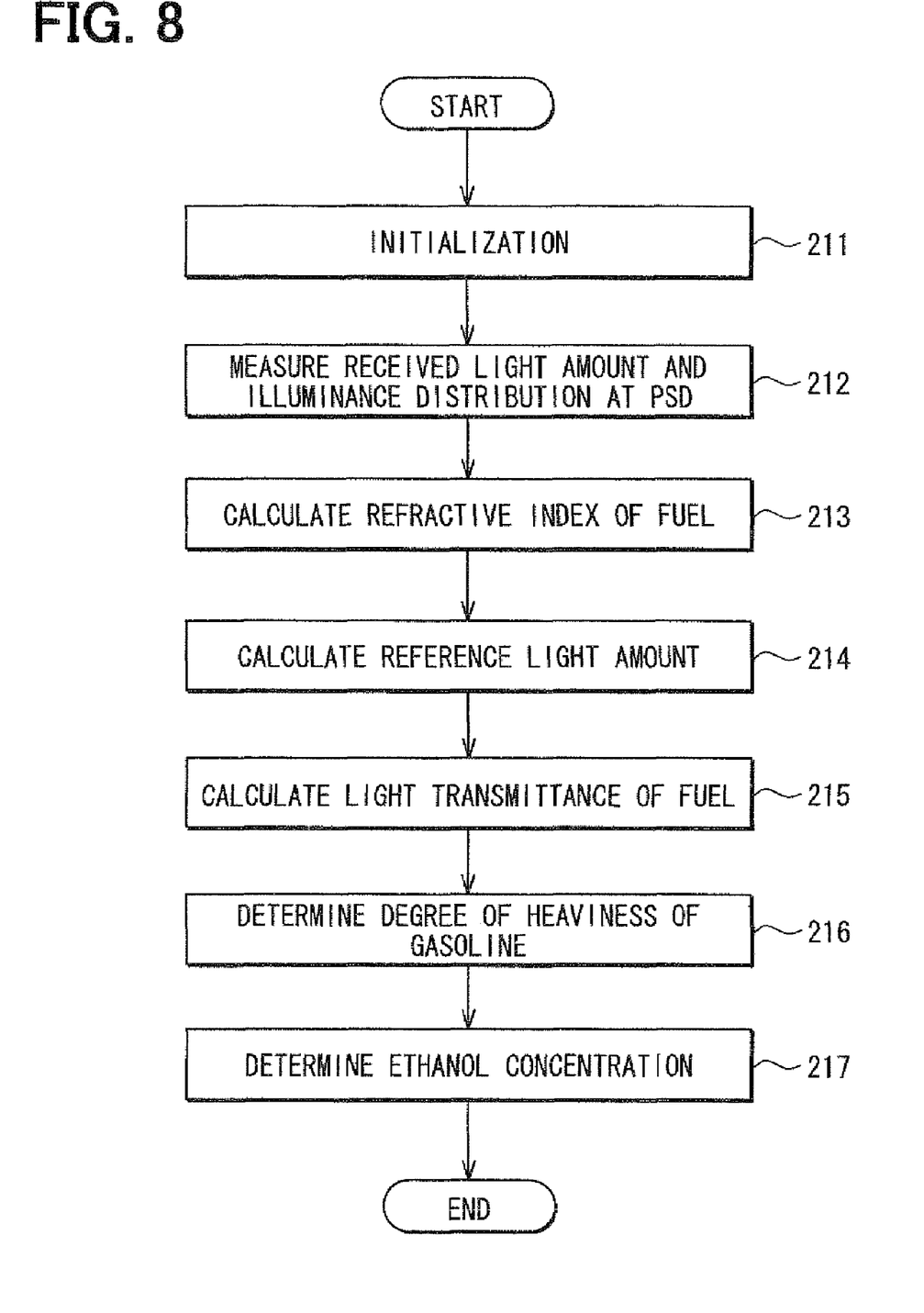
FIG. 8 is a flowchart of another fuel property detection procedure performed by the microcomputer.

Next, the fuel property detection operation performed by the fuel property sensor 1 according to another modified example of the embodiment of the invention will be described below with reference to FIG. 8. In another modified example, like the above-described modified example, the microcomputer 9 is provided to serve as the electric circuit for performing the lighting driving control of the light emitting diode 2, the detection signal processing of a detection signal from the PSD 3, the incident light position calculation processing, and the like. The other modified example differs from the above-described modified example in data stored in the storage means 92 of the computation means 91 as well as the fuel property detection procedure performed by the computation means 91. In the other modified example, the storage area 92 of the computation means 91 previously stores therein data serving as a second map, that is, data about the relationship between the refractive index of the fuel F and the total amount of light received at the PSD 3 when the light transmittance through the fuel F is 100%.

The fuel property detection procedure performed by the computation means 91 will be described below based on the flowchart shown in FIG. 8.

When the ignition switch (switch) of the vehicle 100 is turned ON by a driver's operation, the fuel property sensor 1 starts to be operated, and then the computation means 91 of the microcomputer 9 starts the fuel property detection procedure. The computation means 91 first performs initialization in step S211.

Subsequently, in step S212, the computation means 91 measures the amount of received light and the illuminance distribution (barycenter of receiving the light) at the PSD 3.

Then, in step S213, the computation means 91 calculates the refractive index of the fuel based on the light receiving barycenter of the PSD 3 measured in step S212.

Subsequently, in step S214, the computation means 91 calculates the total amount of light received at the PSD 3 when the light transmittance of the fuel F is 100% based on the refractive index calculated in step S213 and on the second map stored in the storage area 92, that is, data about the relationship between the refractive index of the fuel F and the total amount of light received at the PSD 3 when the light transmittance of the fuel F is 100%.

That is, the expression "total amount of received light at the PSD 3 when the light transmittance of the fuel F is 100%" as used herein means the total amount of light received at the PSD 3 when no fuel F exists in an optical path in which the light emitted from the light emitting diode 2 leads to the PSD 3. The total amount of received light is used as a reference light amount in a calculation process of the light transmittance of the fuel F. Accordingly, the reference light amount can be calculated in step S214.

Next, in step S215, the computation means 91 calculates the light transmittance of the fuel F based on the received light amount at the PSD 3 measured in step S212 and the reference light which is the total amount of light received at the PSD 3 when the transmittance of the fuel F is calculated to be 100% in step S214.

Subsequently, in step S216, the computation means 91 determines the degree of heaviness of the fuel F, that is, the degree of heaviness of the gasoline based on the refractive index of the fuel F calculated in step S213.

Then, in step S217, the computation means 91 determines the ethanol concentration of the fuel F based on the transmittance of the fuel F calculated in step S215.

By the procedure described above, the properties of the fuel F can be accurately determined.

Although the present invention has been fully described in connection with the preferred embodiment and the modified examples thereof with reference to the accompanying drawings, it is to be noted that various changes and modifications will become apparent to those skilled in the art.

In the fuel property sensor 1 according to the embodiment of the invention and the modified examples thereof as described above, the light guiding member 4 is formed of glass, but is not limited thereto. The light guiding member 4 may be formed of any other material that is stable without being discolored and deteriorated even when being immersed in the fuel F to be detected. For example, the light guiding member 4 may be formed of transparent and colorless resin material.

In the fuel property sensor 1 according to the embodiment of the invention and the modified examples thereof as described above, one-dimensional PSD is used as the PSD 3. Alternatively, a two-dimensional PSD may be used as the PSD 3.

Further, in the fuel property sensor 1 according to the one embodiment of the invention and the modified examples thereof as described above, the photoreceptor used is the PSD 3, but is not limited thereto. The photoreceptor may be any other device that can detect a change in optical path of the measurement light due to a change in total reflection angle θA of the reflecting surface 43 together with a change in degree of heaviness of the gasoline. For example, the photoreceptor may have a plurality of photodiodes linearly arranged adjacent to each other.

Although in the embodiment described above, the fuel property sensor 1 is attached to the fuel piping 100 for supplying the fuel F in a fuel tank (not shown) to the engine (not shown), the installation position of the sensor 1 may be any position other than the fuel pipe 100 as long as the light guiding member 4 can be immersed in the fuel F. For example, the sensor 1 may be attached in the fuel tank, or in a fuel rail or the like mounted on the engine for supplying the fuel to an injection valve of each cylinder.

In the fuel property sensor 1 according to the one embodiment of the invention and the modified examples thereof as described above, the light emitting diode 2 used is of a type having a center wavelength of the emitted light of about 1600 nm, but is not limited thereto. When the liquid to be detected is liquid other than ethanol, the light emitting diode may be appropriately changed to another type according to the kind of the liquid. That is, a light emitting diode may be selected which is of a type emitting light with a wavelength that enlarges a difference in light transmittance between the gasoline and liquid of interest for detection of concentration. Furthermore, any light source which is of a type emitting the light with the wavelength described above, other than the above light emitting diode, may be used.

In the fuel property sensor 1 according to the one embodiment of the invention and the modified examples thereof as described above, the fuel F is a liquid mixture of gasoline and ethanol, but may be any other type of fuel. For example, the fuel F may be a liquid mixture of light oil and methanol, an emulsion of heavy oil and water or the like.

Such changes and modifications are to be understood as being within the scope of the present invention as defined by the appended claims.

What is claimed is:

1. A fuel property detection device comprising:
   a light guiding member disposed partially in contact with fuel, the light guiding member being made of a translucent material;
   a light source disposed to allow light emitted therefrom to enter the light guiding member;
   a photoreceptor disposed to receive measurement light which is the light emitted from the light source and proceeding in the light guiding member, the photoreceptor being configured to output a detection signal by receiving the measurement light; and
   a detection portion adapted to detect a property of the fuel based on the detection signal output from the photoreceptor,
   wherein the light guiding member includes a light emitting surface through which the measurement light is emitted from the light guiding member into the fuel, a light incident surface through which the measurement light emitted from the light emitting surface and passing through the fuel enters again the light guiding member, and a reflecting surface at which the measurement light incident from the light incident surface is reflected toward the photoreceptor,
   wherein the light incident surface and the light emitting surface are opposite to each other to have a space between the light emitting surface and the light incident surface in the light guiding member, and
   wherein the space is provided to be filled with the fuel, and the reflecting surface is in direct contact with the fuel.

2. The fuel property detection device according to claim 1, wherein the measurement light passes through the fuel between the light emitting surface and the light incident surface after being emitted from the light source and entering the light guiding member, and then is totally reflected off the reflecting surface to enter the photoreceptor,     wherein the photoreceptor is capable of detecting a total amount of received light and an illuminance distribution at a light receiving area, and     wherein the photoreceptor is disposed to allow the measurement light reflected off the reflecting surface to be incident thereinto.

3. The fuel property detection device according to claim 1, wherein the photoreceptor is a position sensitive detector (PSD).

4. The fuel property detection device according to claim 1, wherein the photoreceptor includes a plurality of phototransistors or photodiodes linearly arranged adjacent to each other.

5. The fuel property detection device according to claim 1, wherein the light source is a light emitting diode.

6. The fuel property detection device according to claim 1, wherein the fuel is a liquid mixture of different kinds of fuel, and a wavelength range of the measurement light is a near-infrared wavelength range.

7. The fuel property detection device according to claim 1, wherein the detection portion includes a storage means for previously storing a first map having a relationship between a refractive index of the fuel and a reflectivity of the reflecting surface, and a computation means for calculating a refractive index of the fuel and a transmittance of the fuel based on the first map stored in the storage means and the detection signal output from the photoreceptor.

8. The fuel property detection device according to claim 7, wherein the computation means further includes: a refractive index calculation means for calculating the refractive index of the fuel based on the detection signal from the photoreceptor; a reflectivity calculation means for calculating the reflectivity on the reflecting surface based on the first map and the refractive index calculated by the refractive index calculation means; and a transmittance calculation means for calculating the transmittance of the fuel based on the reflectivity calculated by the reflectivity calculation means, the detection signal from the photoreceptor, and an amount of light emitted from the light source.

9. The fuel property detection device according to claim 1, wherein the detection portion includes: a storage means for previously storing a second map having a relationship between a refractive index of the fuel and a total amount of light received by the photoreceptor when a transmittance of the fuel is a predetermined value; and a computation means for calculating a refractive index of the fuel and a transmittance of the fuel based on the second map and the detection signal output from the photoreceptor.

10. The fuel property detection device according to claim 9, wherein the computation means includes a refractive index calculation means for calculating the refractive index of the fuel based on the detection signal output from the photoreceptor, and a transmittance calculation means for calculating the transmittance of the fuel based on the second map, the refractive index calculated by the refractive index calculation means, and the detection signal from the photoreceptor.

11. The fuel property detection device according to claim 1, wherein the light emitting surface and the light incident surface are parallel to each other to form the space therebetween in the light guiding member.

12. The fuel property detection device according to claim 11, wherein the light emitting surface and the light incident surface are configured such that an optical axis of the light passing through the light emitting surface and the light incident surface is substantially perpendicular to the light emitting surface and the light incident surface.

13. The fuel property detection device according to claim 1, wherein the space is provided in the light guiding member and is open at the reflecting surface to communicate with a fuel path in which the fuel flows.

14. The fuel property detection device according to claim 1, wherein the fuel is gasoline including alcohol.

15. The fuel property detection device according to claim 14, wherein the detection portion is configured to detect a degree of heaviness of the gasoline and a concentration of the alcohol contained in the gasoline.

* * * * *